US00PP08693P

United States Patent [19]

Nilsson

[11] Patent Number: Plant 8,693

[45] Date of Patent: Apr. 19, 1994

[54] PLUM TREE NAMED 'SUMMER TREAT'

[75] Inventor: Elmer Nilsson, Chico, Calif.

[73] Assignee: Nancy Nilsson, Chico, Calif.

[21] Appl. No.: 972,287

[22] Filed: Nov. 5, 1992

[51] Int. Cl.[5] ..... A01H 5/00

[52] U.S. Cl. ..... Plt./38.1

[58] Field of Search ..... Plt. 38.1

[56] References Cited

U.S. PATENT DOCUMENTS

PP. 2108 12/1961 Swall ..... Plt. 38.1

PP. 2575 11/1965 Garabedian ..... Plt. 38.1

PP. 2619 4/1966 Sumruld ..... Plt. 38.1

*Primary Examiner*—James R. Feyrer

*Assistant Examiner*—Bruce R. Campell

*Attorney, Agent, or Firm*—Bernhard Kreten

[57] ABSTRACT

A plum tree which is of medium to large size, open density, vigorous, upright to spreading-upright, foliated with medium size, obovate and linear, vigorous upright shoots having coarsely crenate margins, mostly globose and occasionally reniform glands which are very small in size, and the stipules are small and very thin with a small percentage remaining on the tree late into the season, blooms abundantly in mid-season with a medium size bud which is conical and quite plump in shape and remaining slightly cupped inwards even at full expansion, white medium flowers, and a regular productive bearer of medium to large, uniform, symmetrically formed, very late ripening clingstone fruit having deep mahogany to a lighter red apple color skin with a range of shades in between, and amber yellow to darker amber flesh, and red pigmentation is present under the skin surface and sometimes deeper. The fruit ripens substantially after the last commercial variety presently grown and has an unusually long harvest season with fruit remaining on the tree in good condition until early September.

1 Drawing Sheet

DISCOVERY OF THE VARIETY

The present new and distinct variety of plum tree was bought by the inventor from a nursery, purportedly as a tree of regular "Santa Rosa" variety. The inventor purchased bareroot grafted stock from the nursery. The tree is from the graft. The graft is visible at the base of the tree. The inventor observed the tree blooming and fruiting uncharacteristically and took particular note of the long harvesting period and the prolonged duration of time the fruit remains on the tree when ripe. Thus, the inventor realized that the tree was substantially different from the regular "Santa Rosa" variety. The inventor coversed with commercial nurserymen who could not identify the new variety as an established variety. The inventor then propagated new trees, which came true to type from the original tree of the new variety.

ASEXUAL REPRODUCTION OF THE VARIETY

A number of plants of the present variety were asexually reproduced from scions obtained from the original tree; scions were grafted by the inventor onto the branches of two existing Santa Rosa plum trees growing on the inventor's property where the original tree is planted. (13010 Hosler Avenue, Chico, Calif. One main branch of each tree is the new variety. The other branches are Santa Rosa. Clones of the original seedling were identical to the parent plant in every distinguishing characteristic.

SUMMARY OF THE VARIETY

The present variety of plum tree is, characteristically, of medium size, excellent vigor, with an upright to upright-spreading structure. The tree is foliated in average quantity with obovate and linear leaves and margins coarsely crenate with relatively large crenations. The leaves are generally medium in size with vigorous upright shoots. The leaf stipules are small and very thin, light green in color and darkening with age. These stipules are semi-deciduous with most stipules falling early in the season, but a small percentage remain attached late into the growing season. The tree blooms in mid-season with white flowers from 15 to 17 mm in diameter when fully expanded. The bloom remains slightly cupped inwards even at full expansion and produces moderately abundant pollen. The tree is productive and a regular bearer of a heavy well set crop of medium to large uniform sized plums of the clingstone variety having amber yellow, firm, dense textured flesh becoming juicy with advanced maturity and a darker amber coloration around the stone. The skin surface is nearly 100 percent colored and is medium to slightly thicker than average. The coloration varies from a deep mahogany to a light apple red with a range of shades in between. Numerous light colored dots are present throughout the fruit surface, most dense on the fruit sides. Dots appearing on the skin are not of a uniform like coloration. The dots are light yellow and light brown. The fruit ripens evenly.

The tree is a vigorous grower, and upright to upright-spreading in growth characteristics. The tree is hardy under typical Sacramento Valley climatic conditions. The trunk is of medium (average) thickness and with rough surface texture and numerous medium sized bark lenticels present; the branch texture varies from moderately rough to nearly smooth. The subject tree was pruned to a vase shaped form. Pollination studies have not been done, but the plant is self-fertile. Good crops have been set a good distance from other varieties and no cross-pollination was required.

The tree blooms in late February in the Butte County. The new variety blooms about 10 days to 2 weeks later than the "Santa Rosa" variety. The tree blooms abundantly with the number of flowers per node ranging from one to four (most frequently two are present). Flower buds are of medium size and medium length. Bud form is conic and quite plump. The buds are slightly appressed to the shoot. The bud surface character is variable with some buds slightly pubescent while others are nearly glabrous. The fruit matures approximately 2 to 4 weeks later than the "Santa Rosa" variety which ripens in mid June in the Chico area. The new variety ripens approximately 2 weeks after the "Santa Rosa" variety in mid to late July (July 23, in 1992). The fruit has an unusually long harvest season with fruit remaining on the tree in good condition until early September.

The long keeping quality results in part from the firm, crisp flesh texture of the new variety in contrast to the regular "Santa Rosa" variety, which softens and becomes watery rapidly both on the tree and in storage. The new variety does not soften and become over ripe on the tree. The ability of the new variety to hang on the tree could greatly extend the availability of these popular type plums to commercial markets as well as furnishing small backyard growers with a plum variety that could be harvested for direct consumption over an extended period from mid to late summer.

BRIEF DESCRIPTION OF THE DRAWING

The drawing is an illustration, by photographic reproduction in color, depicting fruit of the variety. Taken clockwise from the lower left-hand corner, there is depicted: a whole fruit showing its base, a whole fruit showing its apex, a whole fruit showing its suture, a whole fruit taken from a lateral view, a fruit cut in half along its long axis with the stone removed, and the fruit similarly cut in half along its long axis with the stone left in place. The drawing also depicts foliage of the variety, taken clockwise from the upper right-hand corner: a new shoot tip showing coloration, two leaves showing the bottom face, a portion of the current season's growth with the leaves attached, and one leaf of the current season's growth.

DESCRIPTION OF THE VARIETY

The following is a detailed description of the variety of plum tree growing under the ecological condition prevailing near Chico, Butte County, Calif. Color references are to the Maerz and Paul Dictionary of Colors except where terminology having generally accepted meaning is employed.

Tree:
- *Size.*—Medium: 15 ft. height; 12 ft. width.
- *Density.*—Open.
- *Vigor.*—Vigorous, hardy.
- *Age.*—15 years.
- *Rootstock.*—Unknown.

Trunk:
- *Size.*—Medium: 8.5 in.
- *Texture.*—Rough.
- *Lenticels.*—Numerous medium sized bark lenticels; 0.250 mm. length; 0.5 mm. width.
- *Color.*—Dark grey (16-A-1) with occasional hues of dark brown.

Branches:
- *Size.*—Medium (average) in thickness.
- *Texture.*—Varies from moderately rough to nearly smooth.
- *Branching habit.*—Upright to Upright-spreading.
- *Lenticels.*—Numerous: approximately 108 lenticels in 1 cm. of a 5 mm. branch.
- *Color.*—Mature branches range from dark brown (8-L-8) to a lighter brown (7-A-12). The shoots range from a dark green (16-L-7 Bronze Green) with some light hues of brown on the most mature shoots, to a pale green (18-J-5) on the less mature shoots. Immature shoot tips are a light yellow-green color (17-K-3).

Foliage:
- *Quantity.*—Medium: on new growth, approximately 0.20 to 0.25 mm. apart; on one year old growth, leaves occur on short spurs approximately every 6 mm. There are approximately 5 to 10 leaves per spur.

Leaves:
- *Size.*—Medium.
- *Shape.*—Obovate, although leaves approaching oval in form are not uncommon. The leaf tip form is acute with the apex often twisted away.
- *Length.*—14.4 to 16.4 cm.
- *Width.*—5.1 to 5.9 cm.
- *Thickness.*—Average.
- *Texture.*—Smooth.
- *Margin.*—Only slightly undulate. The form is coarsely crenate with relatively large crenations. The crenations are somewhat irregular with double and at time triple crenations present near mid-margin.
- *Petiole.*—16 to 19 mm. in length. 1.5 to 2.0 mm. in thickness. Pale green-yellow color (17-F-4) with somewhat more deep green within the petiole groove.
- *Glands.*—Small in size and variable in form. Most frequently globose, but occasional reniform types can be present. Position is variable with both opposite and alternate position occurring. Color on young leaves is bright green (17-K-5), becoming darker with age.
- *Stipules.*—Small and very thin. 5 to 7 mm. in length. Linear lanceolate form and margins are sparsely serrate. Young stipules are light green (17-H-5), darkening with age. Semi-decidous.
- *Color.*—Upper leaf surface — dark green (24-E-8). Lower leaf surface — light grey-green (23-E-5).

Flower bud:
- *Quality.*—Hardy.
- *Size.*—Medium: at full dormancy, 4 mm.
- *Shape.*—Conic and quite plump, slight appressed to the shoot.
- *Surface.*—Variable, slightly pubescent while others are nearly glabrous.
- *Color.*—Dark brown (8-H-10)(chocolate brown).

Flowers:
- *Size.*—Medium: fully expanded 15 to 17 mm.
- *Color.*—White (1-A-1).
- *Pedicel.*—Moderately long, from 11 to 14 mm. in length. Average thickness, about 1 mm. Pale green color (17-J-5). Glabrous surface.
- *Nectaries.*—Brownish-green (14-F-11) becoming lighter with age to (14-J-8 maple sugar brown).
- *Calyx.*—Glabrous surface. Light brown-green (13-J-1).

Petals:
- *Size.*—Medium: 8 to 10 mm. length; 7 to 9 mm width.
- *Form.*—Ovate to nearly oval. Petal number is five.
- *Claw form.*—Truncate of medium length, averaging about 1 mm.
- *Margins.*—Strongly undulate.
- *Apex.*—Uniform round to slightly domed.

Bloom:
- *Quality.*—Abundant.
- *Date of full bloom.*—March 2nd.

*Authers.*—Medium. Yellow gold (10-K-3lemon yellow) both dorsally and ventrally.

*Stamens.*—6 to 8 mm in length (in relation to the pistil is variable from equal to slightly shorter). White (1-A-1).

*Pollen.*—Moderately abundant. Bright gold yellow (10-L-4 light chrome yellow).

*Pistil.*—8 to 9 mm. in length (including the ovary). Greenish-yellow (17-J-2). Glabrous.

Fruit:

*Maturity.*—When described — Full commercial maturity.

*Date of first picking.*—Jul. 23, 1992.

*Date of last picking.*—Sep. 1, 1992.

*Size.*—Medium to large, cheek diameter 49 to 54 mm, suture diameter 49 to 54 mm. and axial diameter 52 to 58 mm.

*Uniformity.*—Very uniform sizing.

*Form.*—Broadly ovate in lateral aspect, globose in axial aspect. Quite symmetrical.

*Suture.*—Distinct line from base to apex, occasionally slightly folded with the cavity base. Quite smooth, occasionally has a few skin checks. Dark blue coloration (48-J-10).

*Ventral surface.*—Smooth and uniformly rounded with no lipping.

*Cavity.*—Small, moderately deep. 16 to 20 mm width, 19 to 23 mm. length and 9 to 12 mm. depth. A slight amount of skin checking is present within the cavity basin.

*Base.*—Variable, rounded to slightly truncate. The base angle is most frequently very slightly oblique to the fruit axis.

*Apex.*—Somewhat raised, but uniformly rounded. The pistil point is variable from apical to slightly oblique.

*Stem.*—Average to slightly longer than average, 13 to 17 mm. in length. Thickness ranges from 1.5 to 2.0 mm. Olive green (22-K-6 cress green) to a light brown (14-J-7) calabash brown).

Skin:

*Thickness.*—Medium to slightly thicker than average.

*Surface.*—Glabrous with a moderately heavy greay bloom over the entire fruit surface.

*Character.*—Moderately acidic and tenacious to the flesh at commercial maturity.

*Tendency to crack.*—No cracking.

*Color.*—Deep mahogany (8-J-6briarwood) to a lighter apple red (6-L-11 egyptian red) with a range of shades in between. Numerous light colored dots are present through the fruit surface, most dense on the fruit sides (laterally). No ground color is visible.

Flesh:

*Color.*—Amber yellow (10-J-5 corn yellow). A slight amount of red pigmentation is present from 2 to 4 mm under the skin surface and occasionally deeper. The flesh is a darker amber color near the stone (11-K-6 rattan yellow). Numerous short, tender, light colored fibers are present in the flesh.

*Juice.*—Becomes juicy with advanced maturity.

*Texture.*—Firm, dense.

*Ripening.*—Ripens evenly.

*Flavor.*—Sweet, rich flavor with moderate acidity, principally in the skin.

*Aroma.*—Light aroma, pleasant.

*Eating quality.*—Very good.

Stone:

*Adherence to flesh.*—Clingstone. The stone is held tightly in the stone cavity.

*Size.*—Medium. 22 to 26 mm. length, 25 to 17 mm. width and 8.5 to 9.5 mm thickness.

*Form.*—Varible, from oval to nearly ovate.

*Fibers.*—Numerous short, light colored fibers, attached to the stone generally through the stone surface.

*Hilum.*—Very small and a narrow oval in form. Heavily eroded.

*Base.*—Truncate, heavily eroded. Base angle is variable, but most frequently is at right angle to the stone axis.

*Apex.*—Generally rounded, with a short dentate tip.

*Sides.*—Equal or nearly equal in size.

*Dorsal edge.*—A broad deep groove is present on the dorsal edge, extending from the base to about mid-stone. Above mid-stone the groove is much narrower and at times discontinuous. The ridges on each side of the groove are narrow and somewhat jagged. The apical shoulder on the dorsal edge is usually much more rounded than the apical shoulder on the ventral edge, which has a much steeper slope.

*Ventral edge.*—Rounded, 4 to 4.5 mm. thickness at mid-suture. A low wing extends from mid-suture to the base, most prominent near mid-suture.

*Surface.*—Relatively smooth or slightly pebbled with a series of low ridges present basally, converging basally. The most prominent lateral feature is a relatively deep groove extending longitudinally from base to apex, roughly parallel to the ventral suture but 3.5 to 4.5 mm below the edge and converging with the suture both apically and basally. This groove is present on both sides of the stone surface.

*Color.*—Dry stone color is a light buff brown (10-D-4).

*Tendency to split.*—No tendency to split observed.

Use: Fresh market, long distance shipping, as well as small backyard growers for direct consumption.

Keeping quality: Excellent.

Shipping quality: Excellent.

Resistance to insects: No unusual susceptibilities noted.

Resistance to disease: No unusual susceptibilities noted.

Although this novel variety of plum tree possesses the described characteristics under the ecological conditions at Chico, Butte County, Calif., it is to be understood that variation in these characteristics incident to differing climatic and soil condition and cultural practics are anticipated.

I claim:

1. A new and distinct very late ripening variety of a clingstone plum tree having flesh of the amber yellow variety and substantially as herein shown and described, having firm, crisp flesh texture, the fruit having a sweet, rich flavor, being of medium to large size, deep mahogany to a lighter apple red in color with a range of shades in between, and by having a desirable symmetrical shape, where the plum ripens substnatially after other existing commercial varieties, typically in mid to late July and has an unusually long harvest season with fruit remaining on the tree until early September.

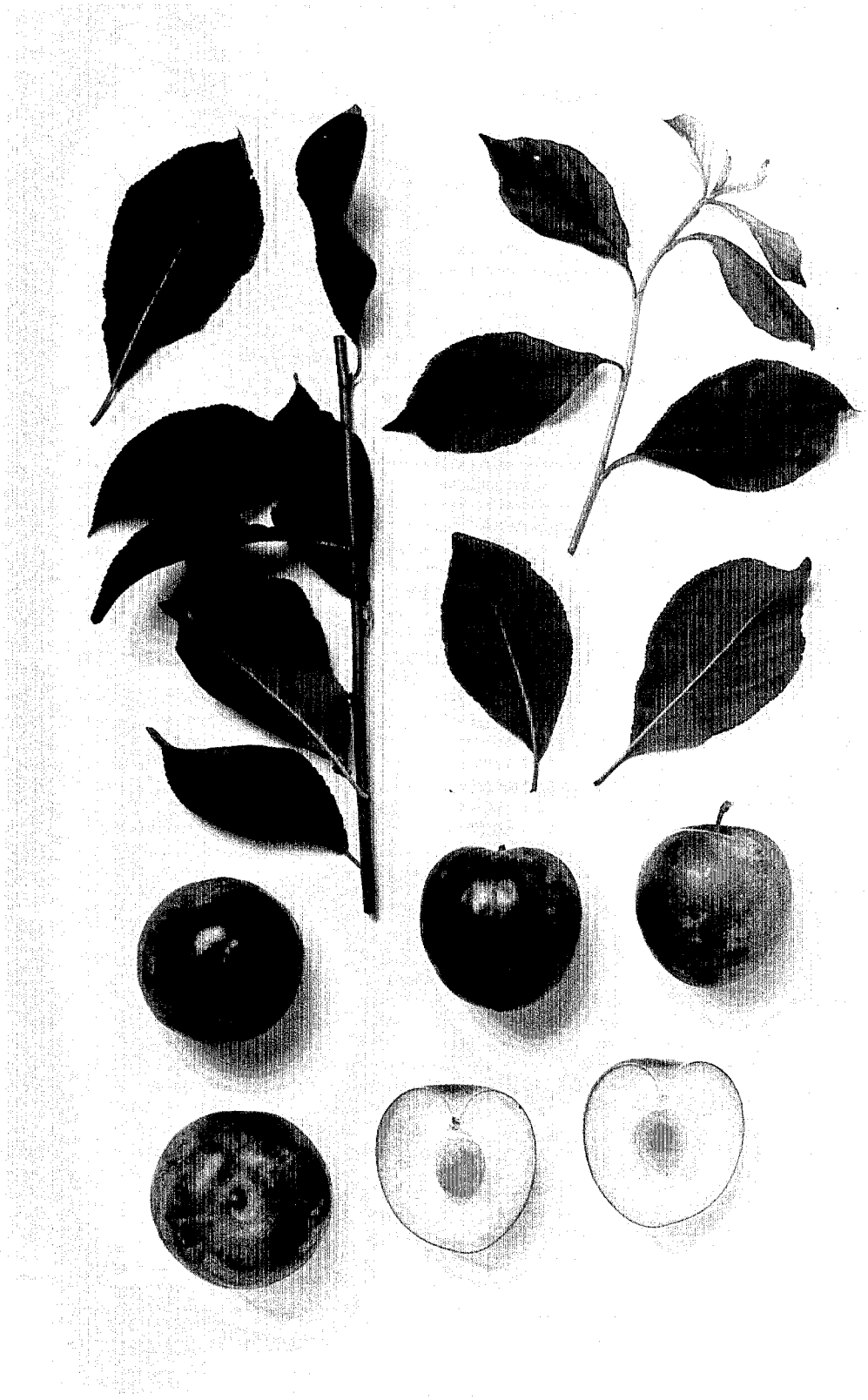

* * * * *